(12) United States Patent
Wichert et al.

(10) Patent No.: US 8,307,724 B1
(45) Date of Patent: Nov. 13, 2012

(54) TWO MODE VAPOR/PARTICULATE SAMPLING DEVICE

(75) Inventors: Clinton Michael Wichert, Edmond, OK (US); Tim Webb, Stillwater, OK (US); Carl Chipman, Stillwater, OK (US); Martin Sanders, Morrison, OK (US)

(73) Assignee: Nomadics, Inc., Stillwater, OK (US)

( * ) Notice: Subject to any disclaimer, the term of this patent is extended or adjusted under 35 U.S.C. 154(b) by 413 days.

(21) Appl. No.: 12/582,380

(22) Filed: Oct. 20, 2009

Related U.S. Application Data

(60) Provisional application No. 61/107,088, filed on Oct. 21, 2008.

(51) Int. Cl.
 *G01N 1/24* (2006.01)
(52) U.S. Cl. ....... 73/864.33; 73/863; 73/864; 73/864.34
(58) Field of Classification Search ............ 73/863, 73/864, 864.33, 864.34
See application file for complete search history.

(56) References Cited

U.S. PATENT DOCUMENTS

| | | | |
|---|---|---|---|
| 2,817,281 A | | 12/1957 | Schwan et al. |
| 3,075,227 A | | 1/1963 | Bowles |
| 3,362,141 A | * | 1/1968 | Royster, Jr. et al. ........ 73/863.23 |
| 4,043,257 A | * | 8/1977 | Aaberg ............................ 454/66 |
| 4,477,986 A | | 10/1984 | Marshall et al. |
| 4,478,096 A | * | 10/1984 | Heiland et al. .............. 73/864.73 |
| 4,570,287 A | | 2/1986 | Kerschner |
| 4,577,489 A | | 3/1986 | Marshall et al. |
| 4,577,490 A | * | 3/1986 | Bray et al. ..................... 73/40.7 |
| 4,607,567 A | | 8/1986 | Esposito |
| 4,718,268 A | * | 1/1988 | Reid et al. .................... 73/19.01 |
| 4,856,419 A | * | 8/1989 | Imai ................................ 454/49 |
| 5,096,467 A | * | 3/1992 | Matsui ............................ 95/269 |
| 5,263,897 A | * | 11/1993 | Kondo et al. ................. 454/189 |
| 5,491,320 A | | 2/1996 | Taylor |
| 5,843,197 A | | 12/1998 | Rossnagel |
| 6,378,385 B1 | * | 4/2002 | Bowers ....................... 73/863.12 |
| 6,632,132 B1 | | 10/2003 | Kikuchi et al. |
| 6,828,795 B2 | * | 12/2004 | Krasnobaev et al. ......... 324/464 |
| 6,888,128 B2 | | 5/2005 | Krasnobaev et al. |
| 8,047,053 B2 | | 11/2011 | Call et al. |
| 2003/0155506 A1 | * | 8/2003 | Motchkine et al. ........... 250/288 |
| 2004/0155181 A1 | * | 8/2004 | Krasnobaev et al. ......... 250/288 |
| 2004/0227073 A1 | * | 11/2004 | Krasnobaev et al. ......... 250/288 |
| 2011/0203931 A1 | * | 8/2011 | Novosselov et al. .......... 204/600 |

FOREIGN PATENT DOCUMENTS

| | | |
|---|---|---|
| EP | 0147916 | 7/1985 |
| JP | 10-185273 | 7/1998 |

OTHER PUBLICATIONS

Daniel Guber, "REEXS—Reinforced Exhaust System Optimization of Operating and Design Parameters", 2002.*
Settles; Sniffers: Fluid-Dynamic Sampling for Olfactory Trace Detection in Nature and Homeland Security—The 2004 Freeman Scholar Lecture; Journal of Fluids Engineering, vol. 127, Mar. 2005; 189-218.

* cited by examiner

*Primary Examiner* — David Rogers
(74) *Attorney, Agent, or Firm* — McAfee & Taft

(57) ABSTRACT

The improved analyte collection device is adjustable between two separate and distinct configurations. The first configuration enhances analyte collection by precluding undesired gas flow from around the sampling device. The second configuration enhances analyte collection by extending and focusing gas flow into the sampling device. Additionally, the current invention provides methods for collecting analyte from the surface of objects or the atmosphere.

42 Claims, 6 Drawing Sheets

TWO MODE VAPOR/PARTICULATE SAMPLING DEVICE

This application claims priority from U.S. Provisional Patent Application Ser. No. 61/107,088 filed on Oct. 21, 2008, the entire contents of which are incorporated herein by reference.

STATEMENT AS TO FEDERALLY SPONSORED RESEARCH

This application was supported in part by a contract from the Air Force, FA8651-05-C0093, and TSA, (HSTS04-04-G-RED943). The United States Government may have rights in and to this application by virtue of this funding.

BACKGROUND OF THE INVENTION

Testing of surfaces for low vapor pressure analytes or particulate analytes is preferably carried out by a "hands off" method. Thus, air gathering systems suitable for collecting the analyte from the surface are preferred. To ensure an adequate quantity of analyte for testing, such systems collect large volumes of air in the region of interest. Preferably, the sampling systems focus the collection of air in the region of interest thereby enhancing the collection of analyte.

SUMMARY OF THE INVENTION

In one embodiment the current invention provides a dual mode sampling device. The sampling device of the current invention comprises a suction assembly having a gas transfer tube carrying a sample tube. The gas transfer tube provides fluid communication between the sample tube and a negative pressure source, e.g. a vacuum pump. The sampling device further comprises a laminar flow assembly having a gas expansion chamber, carrying a vortex vane body and an air inlet port. Additionally, the gas expansion chamber carries the suction assembly. The vortex vane body has at least one air opening passing from the interior to the exterior of the vortex vane body. Alternatively, the vortex vane body may be replaced by a jet generation body having an air opening passing from the interior to the exterior of the jet generation body. The air inlet port is positioned tangentially on the gas expansion chamber and provides fluid communication between the interior and exterior of the gas expansion chamber. Thus, the gas expansion chamber provides fluid communication between the air inlet port and the vortex vane body. The sampling device further includes a vortex generator cone and an actuator mechanism. The actuator mechanism movably secures the vortex generator cone to said sampling device and determines the mode of operation of the sampling device.

In one embodiment, the present invention provides a sampling device suitable for collection vapor and particulate analytes. The sampling device comprises a suction assembly and a laminar flow assembly. The suction assembly comprises a negative pressure source, a gas transfer tube and a sample tube. The gas transfer tube provides fluid communication between the negative pressure source and the sample tube. The laminar flow assembly comprises a positive pressure source, a gas expansion chamber, an air inlet conduit in fluid communication with the gas expansion chamber, and a vortex vane body in fluid communication with the gas expansion chamber. The air inlet conduit provides fluid communication between the positive pressure source and the gas expansion chamber. Additionally, the sampling device includes a vortex generator cone. The vortex generator cone is movable from a first position to a second position.

In another embodiment, the present invention provides a sampling device which generates a stable vortex and is alternatively capable of operating in an Aaberg type configuration. The sampling device comprises a suction assembly and a laminar flow assembly. The suction assembly comprising a negative pressure source, a gas transfer tube and a sample tube. The gas transfer tube provides fluid communication between the negative pressure source and the sample tube. The laminar flow assembly comprises a positive pressure source, a gas expansion chamber, an air inlet conduit in fluid communication with the gas expansion chamber, and a vortex vane body in fluid communication with the gas expansion chamber. The air inlet conduit provides fluid communication between the positive pressure source and the gas expansion chamber. Air outlet openings are carried by the vortex vane body. The ratio of the empty volume defined by the air outlet openings to the volume of the gas expansion chamber is between about 1:18 and about 1:30. Finally, a vortex generator cone is carried by the sampling device. The vortex generator cone is movable from a first position to a second position.

In yet another embodiment, the present invention provides a sampling device which generates a stable vortex and is alternatively capable of operating in an Aaberg type configuration. The sampling device comprises a suction assembly and a laminar flow assembly. The suction assembly comprising a negative pressure source, a gas transfer tube and a sample tube. The gas transfer tube provides fluid communication between the negative pressure source and the sample tube. The laminar flow assembly comprises a positive pressure source, a gas expansion chamber, an air inlet conduit in fluid communication with the gas expansion chamber, and a vortex vane body in fluid communication with the gas expansion chamber. The air inlet conduit provides fluid communication between the positive pressure source and the gas expansion chamber. Air outlet openings are carried by the vortex vane body. The ratio of the cross-sectional area of the air inlet conduit at the gas expansion chamber to the empty volume defined by the air outlet openings is between about 1:2 to about 1:8. Finally, a vortex generator cone is carried by the sampling device. The vortex generator cone is movable from a first position to a second position.

In another embodiment, the current invention provides a method for collecting vapor and particle analytes. The method of the current invention comprises the provision and configuration of the sampling device described above. In the method of the current invention, a pressurized gas passes through the inlet port into the laminar flow assembly and subsequently out the air openings in said vortex vane body. Analyte sample is collected by applying a negative pressure to the suction assembly and using the actuator mechanism to move the vortex generator cone to a first position thereby yielding a planar jet stream from the air opening in the vortex vane body. Subsequently, analyte is collected by applying a negative pressure to the suction assembly and moving the vortex generator cone to a second position thereby generating a vortex having a low pressure area generally centered over the sample tube. Although described as initially collecting analyte with the vortex generating cone in the first position thereby yielding a planar jet stream, the current invention may be initiated with the vortex generator cone in the second position generating a sample isolating vortex centered generally over the sample tube.

DETAILED DISCLOSURE OF THE PREFERRED EMBODIMENTS

Dual Mode Apparatus for Collecting Analyte from a Surface

Figure 1:
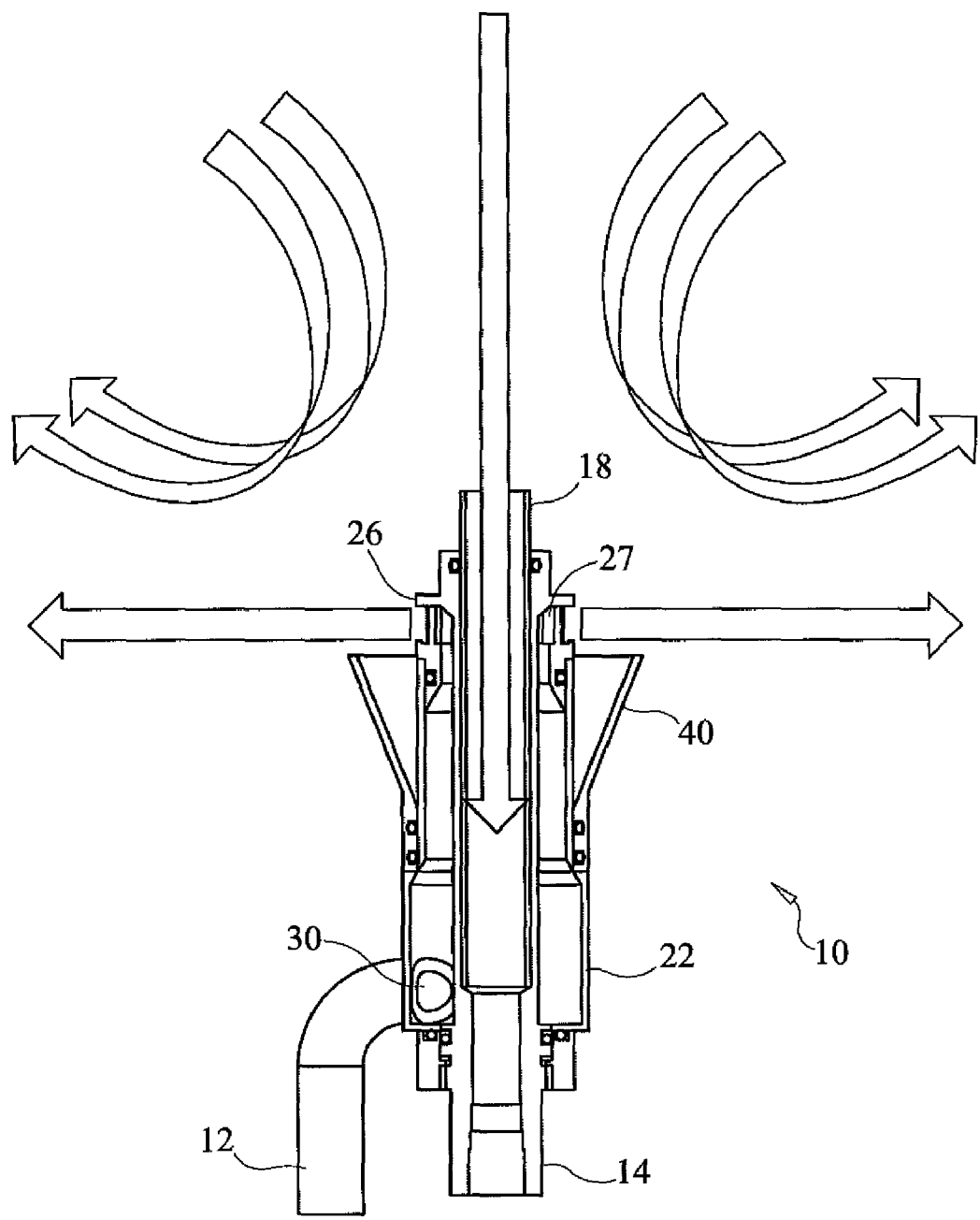
FIG. 1 is a side cut-away view of one embodiment of the current invention with the vortex generator cone in the Aaberg type configuration.
Figure 2:
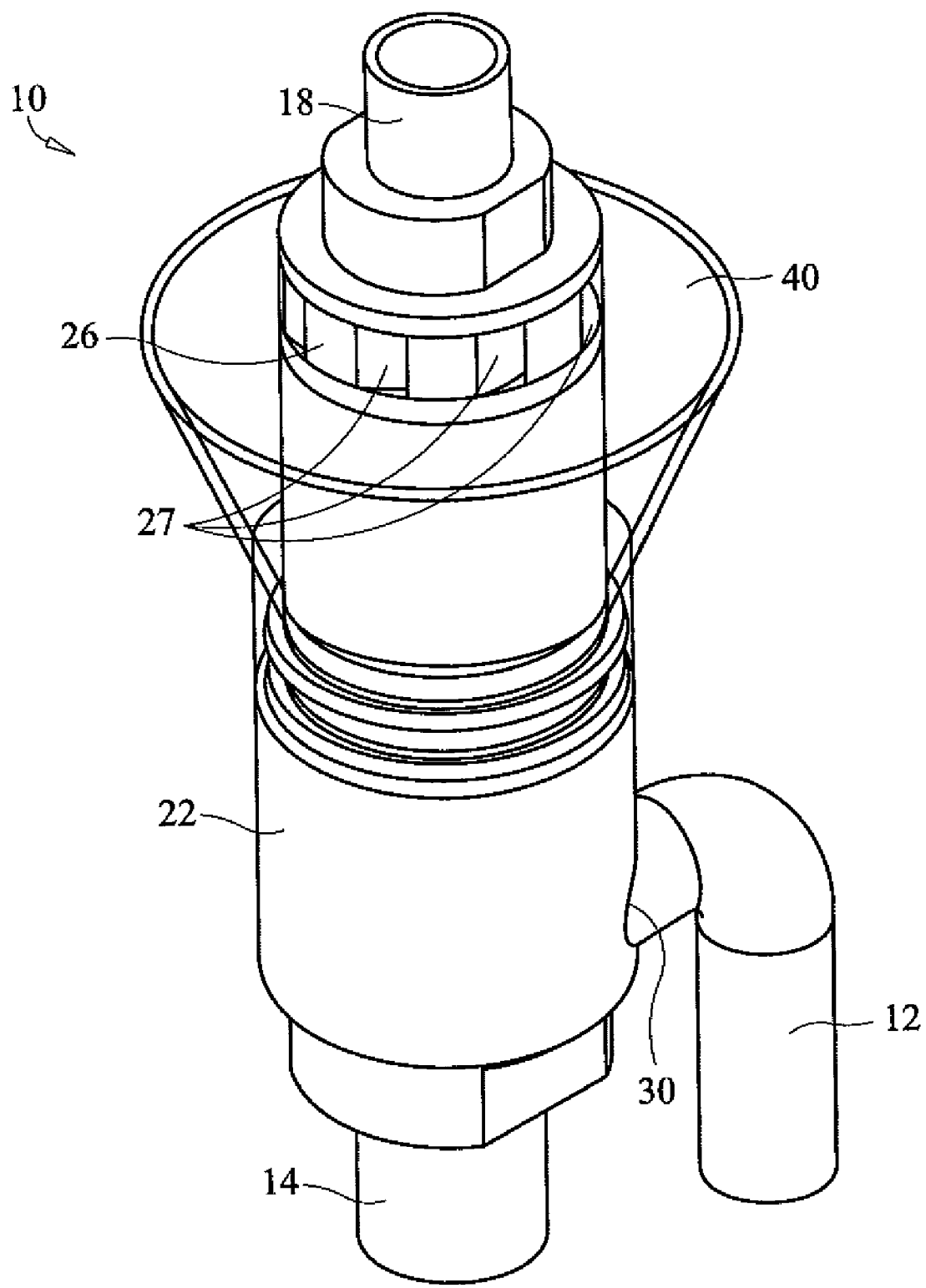
FIG. 2 is a perspective view of the current invention configured as shown in FIG. 1.
Figure 3:
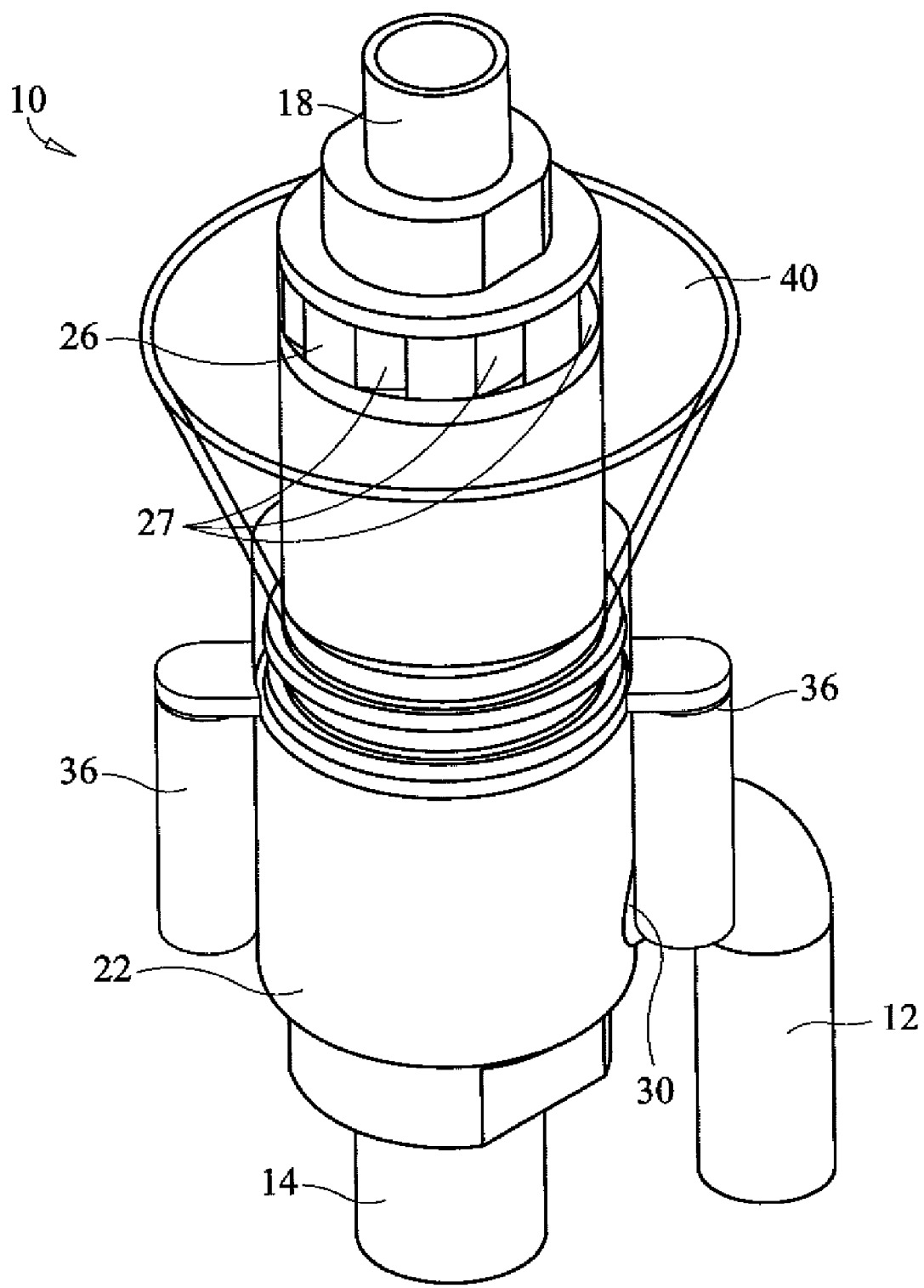
FIG. 3 is a perspective view corresponding to FIG. 2 and incorporating an actuator for moving the vortex generator cone from the Aaberg type position to the vortex position.
Figure 4:
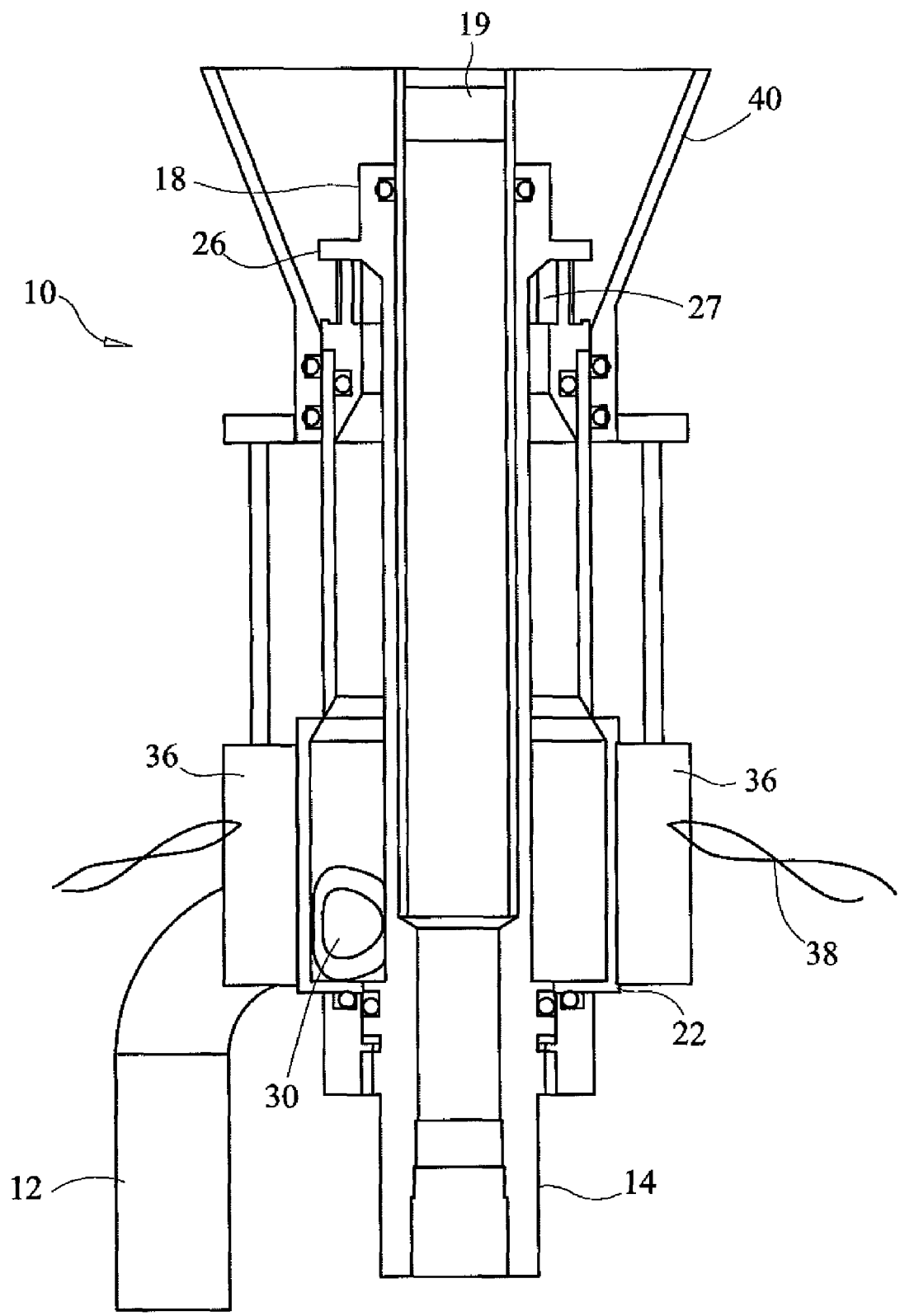
FIG. 4 is a side cut-away view of one embodiment of the current invention with the vortex generator cone in the vortex generation configuration and depicting an actuator for moving the vortex generator cone from the Aaberg type position to the vortex position.
Figure 5:
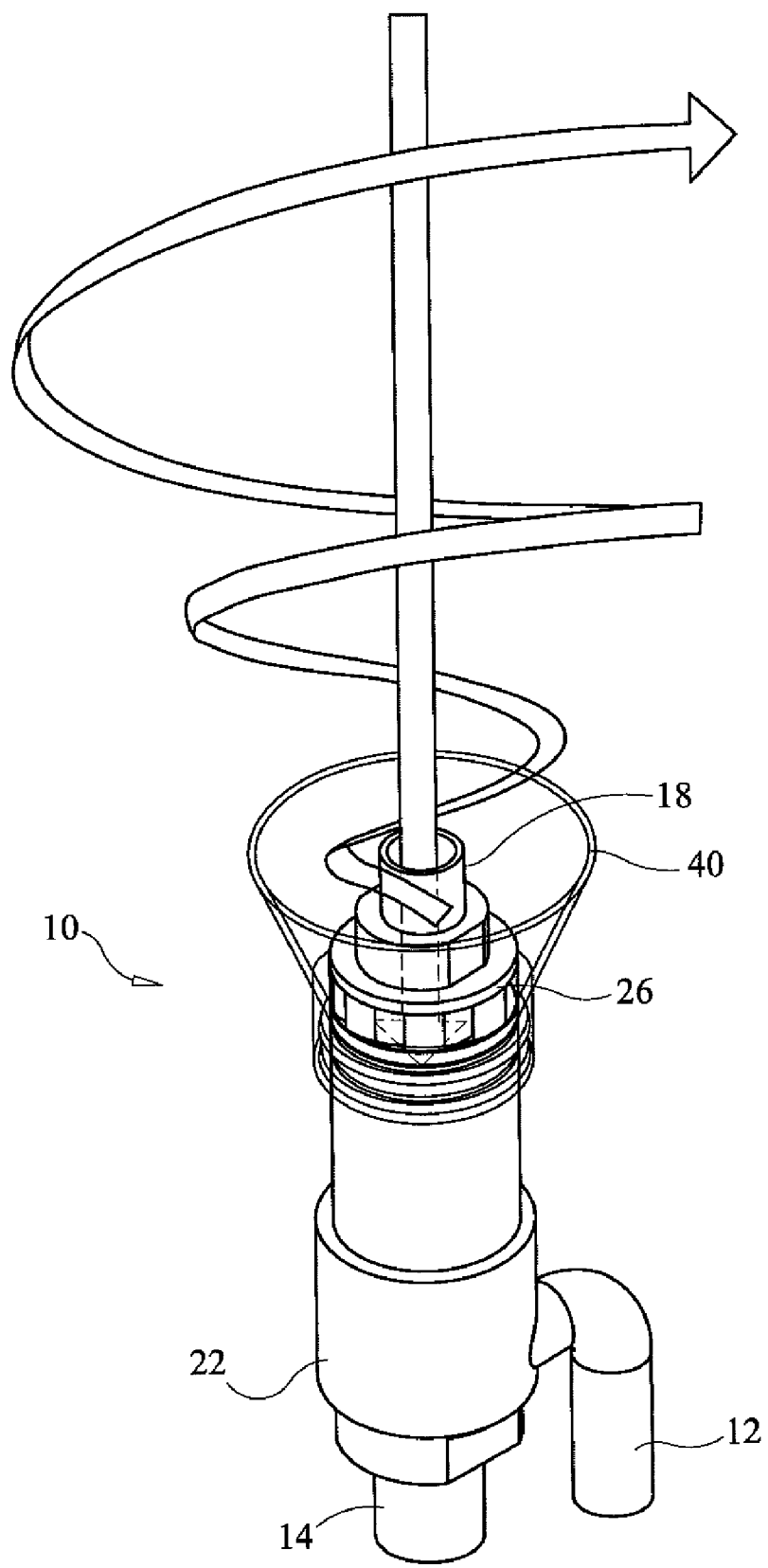
FIG. 5 is a perspective view of the current invention configured as shown in FIG. 2.
Figure 6:
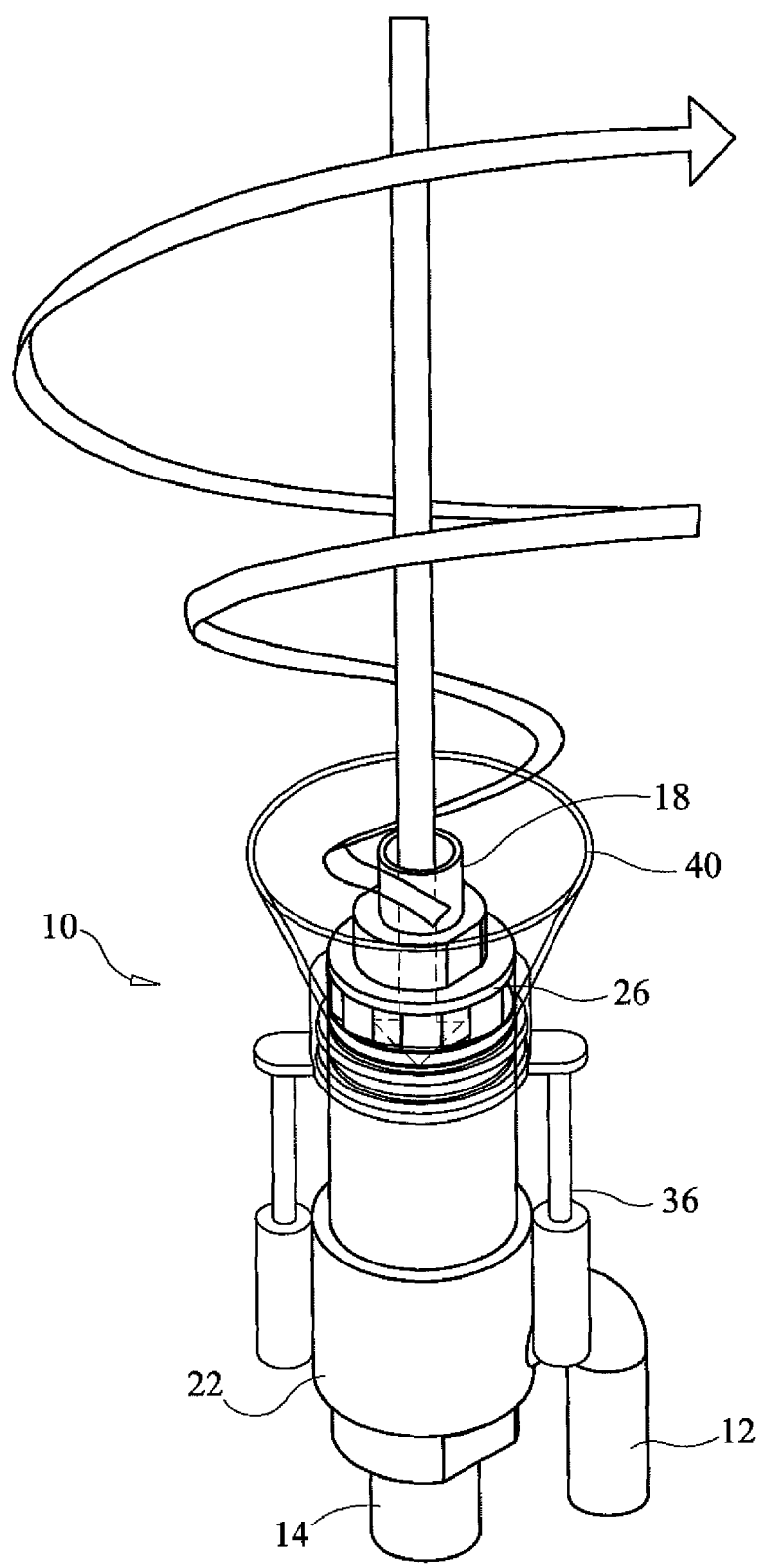
FIG. 6 is a perspective view including a depiction of an actuator for moving the vortex generator cone from the Aaberg type position to the vortex position.

The apparatus of the current invention will be described with reference to FIGS. 1-6. The current invention provides a dual mode sampling device 10 suitable for gathering vapor or particulate analytes from a surface or from the atmosphere. As depicted in FIGS. 1-6, this single sampling device 10 provides two distinct configurations for collecting analyte. FIGS. 1-3 depict sampling device 10 in an Aaberg type configuration. In contrast, FIGS. 4-6 depict sampling device 10 in a vortex generation mode configuration. Additionally, FIGS. 3, 4 and 6 depict a preferred, but optional, actuator mechanism 36 for moving the vortex generator cone 40 from a first position to a second position. Depending upon the gas flow rates through the apparatus and selected configuration, focused analyte sampling is possible at a distance of about 8 to 12 times the nozzle diameter from the apparatus provides.

With continued reference to the drawings, sampling device 10 is commonly associated with at least one and preferably two air pumps (not shown). Typically one air pump operates as a vacuum pump thereby serving as a negative pressure source while the second pump acts as a positive pressure source for sampling device 10. In the preferred embodiment, a gas transfer tube 14 provides fluid communication between the vacuum pump and sampling device 10. Gas transfer tube 14 is in fluid communication with a sample tube 18 centrally located within sampling device 10. Alternatively, a single continuous tube may serve as both sample tube 18 and gas transfer tube 14. Gas transfer tube 14, sample tube 18 and the vacuum pump comprise a suction assembly forming one component of sampling device 10.

A second component of air sampling device 10 is associated with a positive pressure pump and provides the ability to enhance the sampling gathering characteristics of the suction assembly. The second component is referred to as a laminar flow assembly which includes a gas expansion chamber 22, a vortex vane body 26, and an air inlet port 30 associated with air inlet conduit 12. Air inlet port 30 provides fluid communication between the interior and exterior of the gas expansion chamber 22. Thus, air inlet conduit 12 and inlet port 30 provides fluid communication between the positive pressure pump and gas expansion chamber 22. In the preferred embodiment, air inlet port 30 is tangentially positioned on or within gas expansion chamber 22. In this preferred configuration, air inlet port 30 directs the incoming positive pressure flow of air in a swirling manner within gas expansion chamber 22. In the preferred embodiment, about 70 liters per minute to about 120 liters per minute pass flow through the laminar flow assembly while between about 10 liters per minute to about 60 liters per minute pass through the suction assembly.

Vortex vane body 26 has at least two air outlet openings 27 passing from the interior to the exterior of vortex vane body 26. In the preferred embodiment, air openings 27 are vanes or slots 27. Air entering gas expansion chamber 22 passes through vortex vane body 26 exiting sampling device 10 through at least two vanes or slots 27 carried by or in vortex vane body 26.

Preferably, the ratio of the empty volume defined by air outlet openings 27 of vortex vane body 26 to the volume of gas expansion chamber 22 is between about 1:18 and about 1:30. Additionally, the ratio of the cross-sectional area of air inlet conduit 12 at the connection to gas expansion chamber 22 to the outlet flow area defined by air outlet openings 27 of vortex vane body 26 is between about 1:2 and about 1:8. In the preferred embodiment, air inlet port 30 defines the cross-sectional area and provides the fluid connection between air inlet conduit 12 and gas expansion chamber 22. The preferred sampling device 10, configured with the desired ratios, requires about four (4) seconds to establish a vortex at steady state conditions of gas flow through the laminar flow assembly.

In one embodiment, thirty-two air outlet openings 27 are used. However, provided that the above ratios are satisfied, fewer or greater air outlet openings will also operate satisfactorily. The preferred ratios provide the necessary vortex containment, i.e. a stable vortex which does not dissipate upon formation. The indicated ratios permit generation of a stable vortex suitable for dislodging particulate analyte from a surface for collection through sample tube 18. Thus, while the present invention enables operation of Aaberg type collection, the design and operational improvements differ substantially from prior Aaberg devices.

In the preferred embodiment, air outlet openings 27 are tangential slots, i.e. the slots are recessed into vortex vane body 26 such that gas exits vortex vane body 26 tangentially to the exterior surface. Thus, the configuration of tangential slots 27 allows one to operate a single sampling device 10 in two distinct configurations, i.e. positions one and two. In particular, the tangential flow of air in conjunction with the preferred identified ratios and flow rates permits operation of the improved sampling device 10 in both Aaberg type and vortex modes.

The gas expansion chamber 22 supports the primary elements of sampling device 10. As depicted in the Figures, the gas expansion chamber 22 supports the suction assembly, an optional actuator mechanism 36 and a vortex generator cone 40. Actuator mechanism 36 is a binary position control device suitable for moving vortex generator cone 40 from a first position to a second position.

As shown in FIG. 1, vortex generator cone 40 is in the first position, i.e. the Aaberg type configuration. FIG. 4 depicts the vortex generation configuration with the vortex generator cone 40 in the second position. Thus, the position of vortex generator cone 40 determines the nature of the air flowing outward from sampling device 10.

When vortex generator cone 40 is in the first position, air passes out of vortex vane body 26 through slots 27 in a lateral fashion. Although the air exiting slots 27 will be turbulent, the tangential configuration of slots 27 on body 26 yields a laminar flow in the lateral direction. In contrast, when vortex generator cone 40 is in the second position air exits vortex vane body 26 and impacts the interior conical walls of vortex generator cone 40 producing a conical annularly swirling vortex of air. The tangential design of slots 27 in vortex vane body 26 enhances the formation and containment of the resulting vortex.

In the preferred embodiment, actuator mechanism 36 may be any device such as a linear actuator or solenoid, a vacuum diaphragm, a spring operated trigger or other mechanism suitable for moving vortex generator cone 40 from one position to another. Operational control devices (not shown) for controlling the selected actuator mechanism 36 are well known to those skilled in the art. Alternatively a manually operated mechanism for positioning vortex generator cone (not shown) will suffice. When using a manually operated mechanism, the operator will manually move vortex generator cone 40 to the desired position based on the sampling requirements. In the preferred embodiment, vortex generator cone 40 is either in the first or second position as the efficiency of sample collection is negatively impacted by moving the vortex generator cone 40 to positions between the first and second positions.

In the current invention, the solenoid may be employed in a wired or wireless configuration. When used in the wired configuration, the solenoid will be controlled directly with a wire 38 connected to an operator controlled handle or switch (not shown). When provided in a wireless configuration a transmitter will be employed to control the solenoid remotely. The wireless arrangement is particularly suited for use in a robot mounted collector. For example, when using a robot mounted collector the operator will be able to remotely activate sampling device 10 based on camera feedback and detection of suspected analyte target. Further, a sensor such as a range finder to physically detect the distance to the suspected target and an algorithm will allow the robot to "decide" when a suspected target is within range for using the sampling system without operator assistance.

Finally, the preferred embodiment of the current invention utilizes two pumps. However, one skilled in the art will recognize that a single pump providing both vacuum and positive pressure may be adapted for use in the current invention. Further, vacuum reservoirs and pressure tanks may be incorporated to supplement either configuration or replace the pumps.

In the preferred embodiment, vortex generator cone 40 is positioned on sampling device 10 such that sample tube 18 is centrally located within vortex generator cone 40. Further, sample tube 18 preferably contains a pre-concentrator media 19. Pre-concentrator media 19 is selected for its ability to capture the target analyte. Preferably, pre-concentrator media 19 is removable for analysis at a later time. As depicted in FIG. 4, pre-concentrator media 19 is located near the entrance of sample tube 18; however, the location and size of pre-concentrator media 19 may vary without limitation.

Alternatively, sample tube 18 or the optional pre-concentrator media 19 may be connected to a sensor (not shown) suitable for determining the presence of the target analyte. Thus, the current invention is highly flexible and may be adapted to several roles including that of a field sampling mechanism or a field sampling and analyzing mechanism.

Finally, in an alternative embodiment, air outlet openings 27 of vortex vane body 26 may be replaced with a jet ports (not shown) or vortex vane body 26 may be replaced with a jet generation body (not shown) having openings suitable for producing gas jets. In these embodiments, the jet ports will be carried in fluid communication with gas expansion chamber 22 in a similar manner to that provided by vortex vane body 26 and air outlet openings 27. Jet generation body will have a plurality of jet ports (not shown) positioned around its circumference. The jet ports will produce a lateral flow of air when vortex generator cone 40 is in the first position and a vortex when vortex generator cone 40 is in the second position. Preferably, the jet ports are configured to tangentially direct out-flowing gas against the interior wall of vortex generator cone 40 when sampling device 10 is in the second configuration. Further, the tangential arrangement of jets will enhance the laminar flow of air by outwardly directing air when vortex generator cone 40 is in the first position.

Method for Collecting Analyte in Aaberg Type and Vortex Modes

During sampling operations, the configuration of sampling device 10 will be determined by the target analyte and the sampling environment. For example, the first position mode is preferred when collecting vapors and airborne particles in an open environment, such as a tollbooth or ticket collection centers. In this configuration, sampling device 10 directs pressurized gas through air inlet port 30 of laminar flow assembly and out air outlet openings 27 of vortex vane body 26. With vortex generator cone 40 retracted in the first position, the flowing pressurized gas produces an outwardly directed laminar air wall around sample tube 18. This air wall, depicted in FIG. 1 as the two laterally directed arrows, limits and preferably precludes isotropic flow of gas from a low pressure region in the vicinity of the sample tube 18.

During operation of sampling device 10, a vacuum is applied to sample tube 18 using the suction assembly. Thus, the suction assembly draws air into sampling tube 18 from the environment in the direction the sampling device is pointed. With the generation of the air wall, gas flow from behind sample tube 18 is limited and preferably precluded. With reference to FIG. 1, the region behind sample tube 18 corresponds to that below the laterally directed arrows. Thus, the method of the current invention provides for the focused collection of analyte.

In one embodiment of the current invention, pre-concentrator media 19 is located within the interior of sample tube 18. Vapors and particles entering the sampling device are collected on the pre-concentrator media 19 which may be removed and subsequently analyzed to determine the results of the sampling effort.

Alternatively, pro-concentrator media 19 may be omitted and gases entering sampling device 10 will pass directly to an analyzer (not shown) having a suitable sensor for the target analytes of interest. Any conventional analyzer or analyte sensor may be utilized in conjunction with the present invention.

With vortex generator cone 40 in the second position as shown in FIGS. 4-6, the current invention is particularly suited for collecting particle and vapor samples from the surface of the object. Thus, the current invention provides a single sampling device 10 having the ability to change from the Aaberg type configuration to a focusing vortex cone configuration by extending vortex generator cone 40 to the second position.

In the second position, vortex generator cone 40 acts as a gas redirector for slots 27 forcing the flowing gas into a vortex. Formation of the vortex is enhanced by configuring slots 27 to direct the air out of vortex vane body 26 tangentially. Providing a tangential configuration to slots 27 increases the distance the air stream flows prior to contacting the interior wall of vortex generator cone 40 thereby reducing impact turbulence. Gas flows a distance of about 0.050" to about 0.500" after exiting vortex vane body 26 prior to contacting the interior wall of vortex generator cone 40. Thus, the air stream exiting slots 27 will preferably have a contact angle with the vortex generator cone of less than 90 degrees. More preferably, the contact angle will be between about zero and about 45 degrees. The preferred contact angle will be between about 15 and about 45 degrees.

The resulting vortex exiting vortex generator cone 40 produces a low pressure region centered over sample tube 18. During the generation of the vortex, a vacuum is applied to sample tube 18 using the suction assembly. Thus, the suction assembly draws air into sampling tube 18 from the environment in the direction the sampling device is pointed. The resulting low pressure region produced by the vortex focuses collected analyte in the region of the gas flowing into sample tube 18 thereby enhancing analyte collection. Additionally, the resulting vortex aids in removal of particulate matter from the surface of an object.

Accordingly, in this configuration, the resulting vortex can be used to focus the low pressure zone in a desired direction for obtaining analyte samples. When used to generate a vortex, the remaining operational steps are identical to the operations described above with regard to the Aaberg type method.

In one use of the current invention, sampling device 10 may be installed on a remote controlled robot (not shown) and manipulated into a potentially hazardous target zone to test for trace explosives in real-time. In this configuration, sampling device 10 will preferably include actuator 36 to manipulate vortex generator cone 40 between positions one and two. Typically, when gathering samples under these circumstances, sampling device 10 will be incorporated into detector suitable for determining the presence of trace explosives. The robot through either an onboard camera (not shown) or direct visual monitoring will be directed into the zone of interest. As the robot advances on a target surface, sampling device 10 will be operating with vortex generator cone 40 in the first position. If the onboard detector does not report a positive result from the target surface, then vortex generator cone 40 will be moved by actuator 36 to the second position. In this position, a vortex is generated and aimed at the surface to dislodge any trace explosive material. The trace material will be collected by sampling device 10 through nozzle 18 which draws the sample in through an area of negative pressure. When the target zone has a head-space, as may be found in a cargo container, sampling device 10 will be operating with vortex generator cone 40 in the second position, i.e. sampling device 10 generates a vortex.

In another use of the invention, sampling device 10 is attached to a handheld sampling system. This configuration is particularly useful for screening high volume cargo areas such as cargo ports and aircraft shipping terminals. When used as part of a handheld sampling system, sampling device 10 preferably includes a distance measuring device (not shown) such as an ultrasonic distance measuring device or a laser measuring device. When used as part of a handheld device, airflow through sampling device 10 will be actuated in position one when sample tube 18 is within eighteen inches of the target surface. When sampling device 10 is within four to ten inches of the target surface, vortex generator cone 40 will move to position two. Following sampling, pre-concentrator media 19 will be removed and tested for trace analytes such as explosives or drugs.

The current invention has been described predominately with reference to the preferred embodiment and methods of using sampling device 10. However, other embodiments of the current invention will be apparent to those skilled in the art from a consideration of this specification and/or practice of the invention disclosed herein. Accordingly, the foregoing specification is considered merely exemplary of the current invention. The true scope of the current invention is defined by the following claims.

We claim:

1. A sampling device comprising:
a suction assembly and a laminar flow assembly;
said suction assembly comprising a negative pressure source, a gas transfer tube and a sample tube, wherein said gas transfer tube provides fluid communication between said negative pressure source and said sample tube;
said laminar flow assembly comprises a positive pressure source, a gas expansion chamber, an air inlet conduit in fluid communication with said gas expansion chamber, and a vortex vane body in fluid communication with said gas expansion chamber, wherein said air inlet conduit provides fluid communication between said positive pressure source and said gas expansion chamber;
a vortex generator cone carried by said sampling device, said vortex generator cone movable from a first position to a second position.

2. The sampling device of claim 1, further comprising an air pump wherein said air pump acts as said negative pressure source and acts as said positive pressure source.

3. The sampling device of claim 1, further comprising a first air pump acting as said negative pressure source and a second air pump acting as said positive pressure source.

4. The sampling device of claim 1, further comprising pre-concentrator media positioned within said sample tube.

5. The sampling device of claim 1, wherein said gas transfer tube and said sample tube are a single continuous tube.

6. The sampling device of claim 1, wherein said gas expansion chamber supports an actuator mechanism suitable for moving said vortex generator cone from said first position to said second position.

7. The sampling device of claim 6, wherein said actuator mechanism is selected from the group consisting of a solenoid, a vacuum diaphragm and a spring operated trigger.

8. The sampling device of claim 1, wherein said vortex vane body has at least two air outlet openings, wherein said air openings direct air exiting said vortex vane body in a tangential direction.

9. The sampling device of claim 8, wherein said air outlet openings are jet ports.

10. The sampling device of claim 8, wherein the ratio of the empty volume defined by said air outlet openings to the volume of gas expansion chamber is between about 1:18 and about 1:30.

11. The sampling device of claim 8, wherein an air inlet port provides fluid communication between said air inlet conduit and said gas expansion chamber and wherein the ratio of the cross-sectional area of said air inlet conduit at said gas expansion chamber to the empty volume defined by said air outlet openings is between about 1:2 to about 1:8.

12. The sampling device of claim 8, wherein said air outlet openings are slots.

13. The sampling device of claim 12, wherein said slots are recessed into said vortex vane body.

14. A sampling device comprising:
a suction assembly and a laminar flow assembly;
said suction assembly comprising a negative pressure source, a gas transfer tube and a sample tube, wherein said gas transfer tube provides fluid communication between said negative pressure source and said sample tube;

said laminar flow assembly comprises a positive pressure source, a gas expansion chamber, an air inlet conduit in fluid communication with said gas expansion chamber, and a vortex vane body in fluid communication with said gas expansion chamber, wherein said air inlet conduit provides fluid communication between said positive pressure source and said gas expansion chamber;

air outlet openings carried by said vortex vane body, wherein the ratio of the empty volume defined by said air outlet openings to the volume of said gas expansion chamber is between about 1:18 and about 1:30; and, a vortex generator cone carried by said sampling device, said vortex generator cone movable from a first position to a second position.

15. The sampling device of claim 14, further comprising an air pump wherein said air pump acts as said negative pressure source and acts as said positive pressure source.

16. The sampling device of claim 14, further comprising a first air pump acting as said negative pressure source and a second air pump acting as said positive pressure source.

17. The sampling device of claim 14, wherein said gas expansion chamber supports an actuator mechanism suitable for moving said vortex generator cone from said first position to said second position.

18. The sampling device of claim 14, wherein said vortex vane body has at least two air outlet openings, wherein said air openings direct air exiting said vortex vane body in a tangential direction.

19. The sampling device of claim 18, wherein said air outlet openings are slots.

20. The sampling device of claim 18, wherein said air outlet openings are jet ports.

21. The sampling device of claim 18, wherein an air inlet port provides fluid communication between said air inlet conduit and said gas expansion chamber and wherein the ratio of the cross-sectional area of said air inlet conduit at said gas expansion chamber to the empty volume defined by said air outlet openings is between about 1:2 to about 1:8.

22. A sampling device comprising:
a suction assembly and a laminar flow assembly;
said suction assembly comprising a negative pressure source, a gas transfer tube and a sample tube, wherein said gas transfer tube provides fluid communication between said negative pressure source and said sample tube;
said laminar flow assembly comprises a positive pressure source, a gas expansion chamber, an air inlet conduit in fluid communication with said gas expansion chamber, and a vortex vane body in fluid communication with said gas expansion chamber, wherein said air inlet conduit provides fluid communication between said positive pressure source and said gas expansion chamber;
air outlet openings carried by said vortex vane body, wherein the ratio of the cross-sectional area of said air inlet conduit at said gas expansion chamber to the empty volume defined by said air outlet openings is between about 1:2 to about 1:8; and,
a vortex generator cone carried by said sampling device, said vortex generator cone movable from a first position to a second position.

23. The sampling device of claim 22, further comprising an air pump wherein said air pump acts as said negative pressure source and acts as said positive pressure source.

24. The sampling device of claim 22, further comprising a first air pump acting as said negative pressure source and a second air pump acting as said positive pressure source.

25. The sampling device of claim 22, wherein said gas expansion chamber supports an actuator mechanism suitable for moving said vortex generator cone from said first position to said second position.

26. The sampling device of claim 22, wherein said vortex vane body has at least two air outlet openings, wherein said air openings direct air exiting said vortex vane body in a tangential direction.

27. The sampling device of claim 26, wherein said air outlet openings are slots.

28. The sampling device of claim 26, wherein said air outlet openings are jet ports.

29. The sampling device of claim 26, wherein the ratio of the empty volume defined by said air outlet openings to the volume of gas expansion chamber is between about 1:18 and about 1:30.

30. A method of collecting analyte comprising:
providing a sampling device capable of operating in two distinct modes, said sampling device comprising a suction assembly, a laminar flow assembly and a vortex generator cone, said vortex generator cone is movable from a first position to a second position, wherein said first position generates a laminar wall of outwardly flowing air and said second position generates a stable vortex and wherein both positions collect analyte through a central sample tube;
directing gas flow through said laminar flow assembly with said vortex generator cone in the first position while collecting an air sample through said suction assembly;
testing said collected air sample for analyte;
moving said vortex generator cone to said second position, thereby generating a stable vortex and collecting additional air sample from the central region of said vortex through said suction assembly.

31. The method of claim 30, further comprising directing said vortex at a surface for a period of time sufficient to dislodge particles on said surface and subsequently moving said vortex generator cone to said first position and collecting air samples containing said dislodged particles through said suction assembly.

32. The method of claim 30, further comprising the steps of collecting analyte on a pre-concentrator media located within said suction assembly and subsequently analyzing said pre-concentrator media for collected analyte.

33. The method of claim 30, wherein said sampling device is operated in said first position when said sampling device is a distance of about four to about eighteen inches from a surface and wherein said vortex cone generator is moved to said second position when said sampling device is a distance of about four to about ten inches from said surface.

34. The method of claim 30, wherein between about 10 liters per minute to about 60 liters per minute of air pass through said suction assembly and wherein between 7 liters per minute to about 120 liters per minute pass through said laminar flow assembly.

35. A method of collecting analyte comprising:
providing a sampling device capable of operating in two distinct modes, said sampling device comprising a suction assembly, a laminar flow assembly and a vortex generator cone, said vortex generator cone is movable from a first position to a second position, wherein said first position generates a laminar wall of outwardly flowing air and said second position generates a stable vortex and wherein both positions collect analyte through a central sample tube;
positioning said vortex cone generator in the second position;

passing air through said laminar flow assembly under sufficient pressure to generate a stable vortex when said air flow exits said laminar flow assembly and contacts said vortex cone generator;

applying negative pressure to said suction assembly and collecting air samples from the area defined by said resulting vortex;

moving said vortex generator cone to said first position while continuing to pass air through said laminar flow assembly thereby generating a lateral flow of air from said laminar flow assembly;

applying negative pressure to said suction assembly and collecting air samples from the area in front of said sampling device.

36. The method of claim 35, further comprising the steps of collecting analyte on a pre-concentrator media located within said suction assembly and subsequently analyzing said pre-concentrator media for collected analyte.

37. The method of claim 35, wherein between about 10 liters per minute to about 60 liters per minute of air pass through said suction assembly and wherein between 7 liters per minute to about 120 liters per minute pass through said laminar flow assembly.

38. A method of collecting analyte comprising:

providing a sampling device capable of operating in two distinct modes, said sampling device comprising a suction assembly, a laminar flow assembly and a vortex generator cone, said vortex generator cone is movable from a first position to a second position, wherein said first position generates a laminar wall of outwardly flowing air and said second position generates a stable vortex and wherein both positions collect analyte through a central sample tube;

alternating the position of said vortex cone generator from said first position to said second position while passing air through said laminar flow assembly;

applying negative pressure to said suction assembly; and, using pre-concentrator media positioned within said suction assembly to collect analyte from air samples passing through said suction assembly.

39. The method of claim 38, wherein said step of alternating the position of said vortex cone generator is carried out by an actuator mechanism in response to an electronic signal.

40. The method of claim 38, wherein when said sampling device is a distance of about four to about eighteen inches from a surface said vortex cone generator is in said first position and wherein said vortex cone generator is moved to said second position when said sampling device is a distance of about four to about ten inches from said surface.

41. The method of claim 40, wherein said vortex cone generator is subsequently moved to said first position.

42. The method of claim 40, wherein between about 10 liters per minute to about 60 liters per minute of air pass through said suction assembly and wherein between 7 liters per minute to about 120 liters per minute pass through said laminar flow assembly.

* * * * *